(12) United States Patent
Geller

(10) Patent No.: US 7,923,571 B2
(45) Date of Patent: Apr. 12, 2011

(54) PROCESS FOR PREPARING SUBSTITUTED 2-ALKOXYCARBONYL-3-AMINOTHIOPHENES

(75) Inventor: Thomas Geller, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 754 days.

(21) Appl. No.: 11/722,506

(22) PCT Filed: Dec. 14, 2005

(86) PCT No.: PCT/EP2005/013406
§ 371 (c)(1),
(2), (4) Date: Jun. 21, 2007

(87) PCT Pub. No.: WO2006/072375
PCT Pub. Date: Jul. 13, 2006

(65) Prior Publication Data
US 2010/0004130 A1    Jan. 7, 2010

(30) Foreign Application Priority Data

Dec. 29, 2004    (DE) .......................... 10 2004 063 191

(51) Int. Cl.
*C07D 333/36*    (2006.01)
(52) U.S. Cl. ....................................................... 549/68
(58) Field of Classification Search ....................... 549/68
See application file for complete search history.

(56) References Cited

U.S. PATENT DOCUMENTS 5,166,346 A    11/1992    Rippel et al.

FOREIGN PATENT DOCUMENTS

| DE | 27 37 738 | 3/1978 |
| EP | 0 331 919 | 9/1989 |
| GB | 1 587 084 | 3/1981 |
| WO | 03/062221 | 7/2003 |

OTHER PUBLICATIONS

P.N. Confalone, et al., "A total Synthesis of Biotin Based on Derivates of 2,5-Dihydrothiophene[1a]", J. Org. Chem., vol. 42, No. 9, 1997, pp. 1630-1633.
D.L. Schmidt, et al., "Reactions of the Chlorine Complex of Tetrahydrothiophene", J. Org. Chem., vol. 50, 1985, pp. 2840-2847.
P.G. Gassman, et al., "Use of Halogen-Sulfide Complexes in the Synthesis of Indoles, Oxindoles, and Alkylated Aromatic Amines", Journal of American Chemical Society, 95:19, Sep. 19, 1973, pp. 6508-6509.

*Primary Examiner* — Taofiq A Solola
(74) *Attorney, Agent, or Firm* — Baker Donelson Bearman, Caldwell & Berkowitz, PC

(57) ABSTRACT

The present invention relates to a process for preparing 4-alkoxycarbonyl-3-aminothiophenes of the general formula (I)

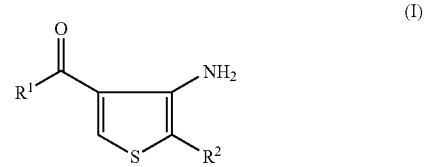

and/or their hydrochlorides of the formula (I)'

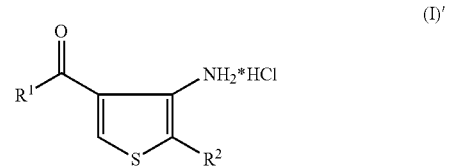

in which $R^1$ and $R^2$ are each as defined in the description, and/or their mono- or bisacetylated or mono- or bisformylated form,
by reacting enamines of the formula (II)

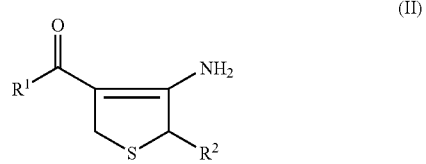

in which $R^1$ and $R^2$ are each as defined in the description, and/or their mono- or bisacetylated or mono- or bisformylated form,
with a chlorinating agent in the presence of one or more diluents, and also to a process for preparing the compounds of the formula (II).

16 Claims, No Drawings

PROCESS FOR PREPARING SUBSTITUTED 2-ALKOXYCARBONYL-3-AMINOTHIOPHENES

CROSS-REFERENCE TO RELATED APPLICATIONS

This is a §371 National Stage Application of International Application No. PCT/EP2005/013406 filed Dec. 14, 2005, which claims priority from German Application No. German Application No. 10 2004 063 191.3 filed Dec. 29, 2004.

BACKGROUND OF THE INVENTION

1. Field of the Invention

The invention relates to a novel process for preparing substituted 4-alkoxycarbonyl-3-aminothiophenes which are known as intermediates for active ingredients in agriculture, especially for substituted, herbicidally active thienylaminocarbonyltriazolinones (cf. WO 01/05788).

2. Description of Related Art

It is known that substituted 4-alkoxycarbonyl-3-aminothiophenes can be prepared by oxidation with hydrogen peroxide and subsequent acidic workup (EP-A 331 919). However, the achievable yields in these processes are not entirely satisfactory. It has further been stated that 4-alkoxycarbonyl-3-aminothiophenes are prepared by reacting 3-oxatetrahydrothiophenes with an acid addition salt of hydroxylamine, and the resulting oximes can be treated with an acid (DE-A 27 37 738) or converted in situ to the corresponding amine hydrochlorides. However, a disadvantage of this reaction is the observed occurrence of decarboxylated amine as an undesired by-product, complicated purification and the need to use the hydroxylamine acid addition salt in a large excess.

SUMMARY OF THE INVENTION

The preparation of the substituted 4-alkoxycarbonyl-3-aminothiophenes by another route with higher yield and efficiency is therefore desirable.

It has now been found in accordance with the invention that the preparation of the substituted 4-alkoxycarbonyl-3-aminothiophenes succeeds in high yield when 3-oxatetrahydrothiophenes are reacted with ammonium acetate or ammonium formate to give the corresponding enamines. This reaction surprisingly succeeds even with catalytic amounts of the salts when ammonia is added additionally. Only with ammonia and without the salt addition, no significant conversion to the enamines takes place. The enamines are then reacted with chlorinating agents such as sulfuryl chloride or chlorine. Surprisingly, the product formation proceeds without significant formation of by-products, even though it is known from the literature that tetrahydrothiophenes react, for example, with sulfuryl chloride under S-chlorination and form chlorine complexes (for example sulfonium salts) (JACS, 1973, 95, 6508-6509). These compounds are highly reactive and can, for example, react with aromatic amines (JACS, 1973, 95, 6508-6509) or polymerize (J. Org. Chem., 1985, 50, 2840-2847).

It has accordingly been found that 4-alkoxycarbonyl-3-aminothiophenes of the general formula (I)

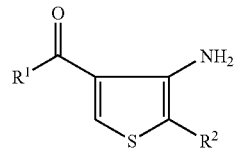

and/or their hydrochlorides of the formula (I)'

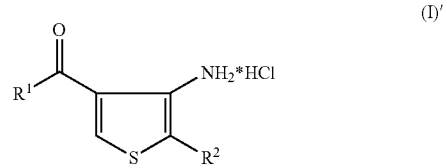

and/or their mono- or bisacetylated or mono- or bisformylated form of the formulae (I)''

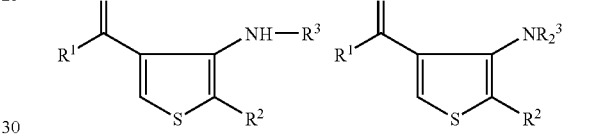

in which
$R^1$ is optionally halogen- or $C_1$-$C_4$-alkoxy-substituted alkoxy having from 1 to 6 carbon atoms,
$R^2$ is optionally halogen- or $C_1$-$C_4$-alkoxy-substituted alkyl having from 1 to 6 carbon atoms or in each case optionally halogen-, $C_1$-$C_4$-alkyl- or $C_1$-$C_4$-alkoxy-substituted aryl or arylalkyl having in each case 6 or 10 carbon atoms in the aryl group and, if appropriate, from 1 to 4 carbon atoms in the alkyl moiety, and
$R^3$ is acyl or formyl,
are obtained in very good yields and in high purity
when enamines of the formula (II)

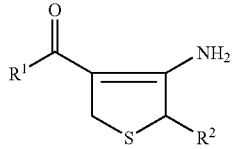

and/or their mono- or bisacetylated or mono- or bisformylated form of the formula (II)''

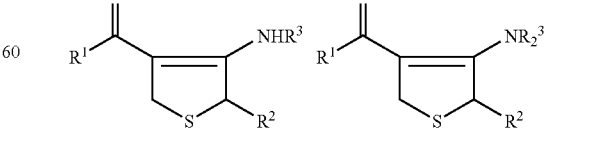

in which $R^1$, $R^2$ and $R^3$ are each as defined above
are reacted with a chlorinating agent in the presence of one or more diluents.

In the formula (I), $R^1$ is preferably $C_1$-$C_4$-alkoxy, in particular methoxy, ethoxy, n- or i-propoxy. $R^2$ is preferably $C_1$-$C_4$-alkyl, in particular methyl, ethyl, n- or i-propyl.

The process according to the invention is particularly advantageously suitable for preparing 2-methyl-3-amino-4-methoxycarbonylthiophene of the formula (Ia)

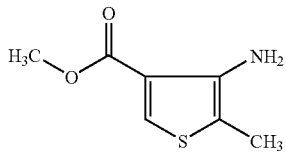

(Ia)

or its hydrochloride of the formula (Ia)'

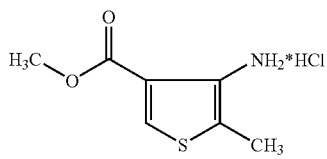

(Ia)' or its mono- or bisacetylated or mono- or bisformylated form (Ia)"

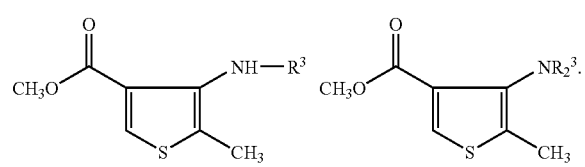

(Ia)"

In the process according to the invention, generally no auxiliary base addition is necessary.

DETAILED DESCRIPTION OF A PREFERRED EMBODIMENT

In the reaction of the enamines with a chlorinating agent, a novel process has surprisingly been found which allows the preparation of the 4-alkoxycarbonyl-3-aminothiophenes in very good yields and in high purity with a short reaction time.

In a preferred embodiment, the reaction product is formed rapidly and with high yield. After the reaction, the product can be isolated in a very simple manner by precipitating as the hydrochloride from an organic solution with water and subsequent filtration. Alternatively, a product isolation in the case of use of sulfuryl chloride or chlorine gas can also be effected by simply removing the solvent and the excess oxidizing agent under reduced pressure. High excesses of expensive reagents are not needed for the product preparation.

The process according to the invention thus constitutes an enrichment of the prior art, since it allows a very advantageous preparation of substituted 4-alkoxycarbonyl-3-aminothiophenes. This facilitates access to the herbicidal thienylaminocarbonyltriazolinones based on these intermediates.

The enamines of the formula (II) to be used as starting compounds in the process according to the invention are preferably obtained by reacting compounds of the formula (III)

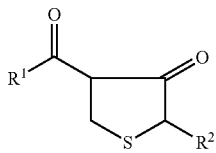

(III)

in which $R^1$ and $R^2$ are each as defined above
with ammonium formate, optionally in the presence of $NH_3$, with ammonium acetate, optionally in the presence of $NH_3$, with a mixture of formic acid and $NH_3$ and/or with a mixture of acetic acid and $NH_3$ in the presence of one or more diluents.

However, the compounds of the formula (II) may also be prepared as specified in EP-A 331 919. They may additionally be prepared by processes known in principle (see, for example, J. Org. Chem. Vol. 42, No. 9, 1977).

The amines of the formula (II) may be acetylated or formylated in a conventional manner to the corresponding compounds of the formula (II)".

The compounds of the formula (III) are known and can be prepared, for example, by the process specified in DE-A 27 37 738.

The inventive reaction of the substituted enamines with a chlorinating agent is performed generally at temperatures between −15° C. and 70° C., preferably between −15° C. and 25° C., more preferably between −10° C. and 0° C. The diluents used in the reaction are preferably halogenated aromatic or aliphatic hydrocarbons. Methylene chloride and chlorobenzene are particularly preferred as diluents.

In the inventive reaction of the substituted enamines with a chlorinating agent, the reaction times are generally between 1 minute and 6 hours, preferably between 2 and 120 minutes. The reactant is generally initially charged in the diluent at a concentration of from 11 to 50% by weight, preferably 20-30% by weight.

To carry out the process according to the invention, the compounds of the formula (I) are prepared preferably by using the reagent in excess. In general, between 0.8 and 10 mol, preferably between 1.0 and 1.1 mol, of the chlorinating agent are used per mole of enamine of the formula (II).

The chlorinating agent used in the process according to the invention may be (elemental, gaseous) chlorine or sulfuryl chloride ($SO_2Cl_2$). It is also possible to use other compounds which readily release chlorine. Particular preference is given to the use of sulfuryl chloride.

The process according to the invention is generally carried out under standard pressure. However, it is also possible to carry out the process according to the invention under elevated or reduced pressure, generally between 0.1 bar and 10 bar.

The preparation of the enamines of the formula (II) from the compounds of the formula (III) is performed generally at temperatures between 20° C. and 118° C., preferably between 50° C. and 118° C.; more preferably at reflux temperature of the diluent in question. Suitable diluents are neutral organic solvents, for example $C_1$-$C_4$-alcohols, in particular methanol, ethanol, or else polar organic solvents, for example acetone or acetonitrile. The diluents used may also be diluents which are used in the subsequent reaction with the chlorinating agents in mixtures with the aforementioned diluents. Particular preference is given to the use of methanol and ethanol.

In the conversion of the compounds of the formula (III) to give the enamines of the formula (II), the reaction times are generally between 30 minutes and 12 hours, preferably between 20 and 240 minutes.

To carry out the process for preparing the compounds of the formula (II), preference is given to using the reagent in excess. In general, between 0.8 and 10 mol, preferably between 1.2 and 3.0 mol, of the reagent, for example ammonium formate or acetate, are used per mole of the compound of the formula (III).

Alternatively, the ammonium formate or acetate may also be used in catalytic amounts when $NH_3$ is metered in during the reaction time. In that case, preferably 0.1-0.8 mol of the ammonium salt in question (or of a mixture of the two) and from 1 to 3 mol of $NH_3$ are used per mole of reactant.

When the reagent used in this reaction is not directly ammonium formate or acetate, but rather a mixture of acetic acid and $NH_3$ or formic acid and $NH_3$, preferably from 0.1 to 1 mol of acid and from 1 to 3 mol of $NH_3$ are used per mole of reactant.

The process for preparing the compounds of the formula (II) from those of the formula (III) is generally carried out under standard pressure. However, it is also possible to carry out the process under elevated or reduced pressure, generally between 0.1 bar and 10 bar.

The enamines of the formula (II) prepared from the compounds of the formula (III) can be isolated before they are used in the inventive process step. However, it is also possible to react the resulting compounds further with the chlorinating agent directly without intermediate isolation after partial, but preferably full, exchange of the diluent.

The present invention also provides a combination of the inventive process step with the above-specified process step for preparing the starting compounds of the formula (II). Also in accordance with the invention is the process step for preparing the starting compounds of the formula (II) alone, which is particularly suitable for obtaining the compounds of the formula (II) in high yields.

It has accordingly been found that 4-alkoxycarbonyl-3-aminothiophenes of the general formula (I)

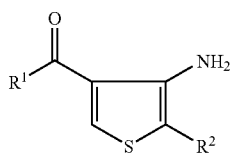

(I)

and/or their hydrochlorides of the formula (I)'

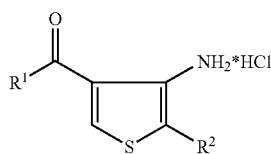

(I)' and/or their mono- or bisacetylated or mono- or bisformylated form of the formulae (I)"

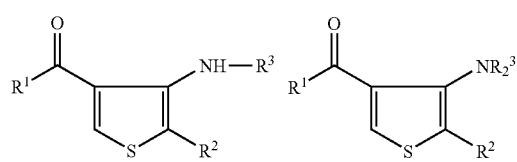

(I)"

in which
$R^1$ is optionally halogen- or $C_1$-$C_4$-alkoxy-substituted alkoxy having from 1 to 6 carbon atoms, $R^2$ is optionally halogen- or $C_1$-$C_4$-alkoxy-substituted alkyl having from 1 to 6 carbon atoms or in each case optionally halogen-, $C_1$-$C_4$-alkyl- or $C_1$-$C_4$-alkoxy-substituted aryl or arylalkyl having in each case 6 or 10 carbon atoms in the aryl group and, if appropriate, from 1 to 4 carbon atoms in the alkyl moiety, and $R^3$ is acyl or formyl, are obtained in very good yields and in high purity when compounds of the formula (III)

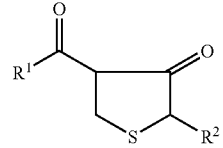

(III)

in which $R^1$ and $R^2$ are each as defined above
are reacted with ammonium formate, optionally in the presence of $NH_3$, with ammonium acetate, optionally in the presence of $NH_3$, with a mixture of formic acid and $NH_3$ and/or with a mixture of acetic acid and $NH_3$ in the presence of one or more diluents,
and the resulting compounds of the formula (II)

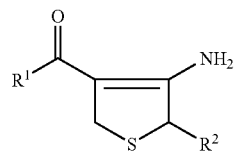

(II)

in which $R^1$ and $R^2$ are each as defined above
are converted, directly or after subsequent acetylation or formylation, to a compound of the formula (II)"
with a chlorinating agent in the presence of one or more diluents.

PREPARATION EXAMPLES

Example 1

Preparation of the Precursor of the Formula (II)

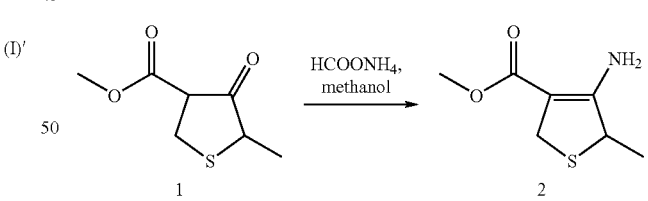

38.1 g of 1,4-anhydro-2,5-dideoxy-2-(methoxycarbonyl)-1-thiopent-3-ulose (1, 0.2 mol, content: 91.5%) and 37.9 g of ammonium formate (0.6 mol) were initially charged in 330 ml of methanol and subsequently heated to reflux temperature for 15 h. The solvent was distilled off under reduced pressure and the residue taken up in 200 ml of water. After extraction with 2×200 ml of $CH_2Cl_2$, drying of the combined organic phases ($Na_2SO_4$) and distilling of the solvent, 37 g of methyl 4-amino-5-methyl-2,5-dihydrothiophene-3-carboxylate (2) were obtained (97% of theory, content: 91%, m.p.: 60° C., $^1$H NMR (400 MHz, $d^3$-$CD_3CN$): 1.46 (d, 3H, J=6.8 Hz), 3.63 (dd, 1H, $J_1$=12 Hz, $J_2$=0.9 Hz), 3.64 (s, 3H), 3.76 (dd, 1H, $J_1$=12 Hz, $J_2$=3.5 Hz), 4.11-4.19 (m, 1H)).

Example 2

Preparation of the Precursor of the Formula (II)

20 g of 1,4-anhydro-2,5-dideoxy-2-(methoxycarbonyl)-1-thiopent-3-ulose (1, 87 mmol, content: 72.6%) and 3.6 g of ammonium acetate (44 mmol) were initially charged in 55 ml of methanol. The reaction mixture was heated to reflux for 2 h. Subsequently, 1.8 g of ammonia gas (105 mmol) were introduced at reflux temperature over a period of 30 min. The reaction mixture was then stirred under reflux for a further 7 h. For workup, the procedure was analogous to example 1. 19.3 g of methyl 4-amino-5-methyl-2,5-dihydrothiophene-3-carboxylate (2) were obtained (96% of theory, content: 73.6%).

Example 3

Preparation of the Precursor of the Formula (II)

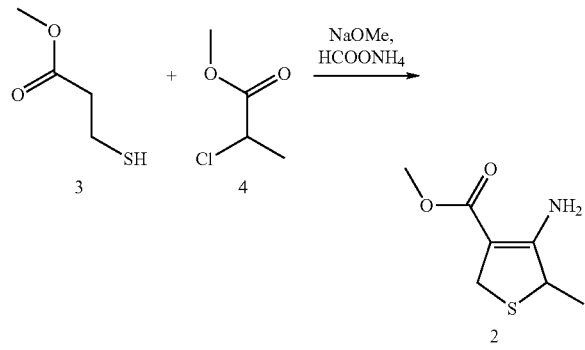

At 0-10° C., 61.3 g of methyl 3-mercaptopropionate (3, 0.5 mol, content: 98%) were added dropwise over 35 min to 90 g of a 30% solution of NaOMe in methanol (0.5 mol). After the addition, the mixture was stirred at 0-10° C. for a further 10 min and subsequently, at 0-5° C., 63.2 g of methyl 2-chloropropionate (4, 0.5 mol, content: 97%) were metered in over 50 min. The reaction mixture was stirred at 0-5° C. for a further 30 min, before 500 ml of xylene were added. Subsequently, the methanol was substantially distilled off. 99 g of a 30% solution of NaOMe in methanol (0.55 mol) were added dropwise at approx. 90° C. over 75 min to the resulting suspension, and methanol continued to be distilled off at the same time. The reaction mixture was then cooled to 80° C. under argon before 33 g of acetic acid (0.55 mol) were metered in. On completion of addition, 500 ml of water were added at 70° C. and the mixture was subsequently cooled to room temperature. After the separation of the phases, the aqueous phase was reextracted once more with 250 ml of xylene and the combined organic phases were subsequently washed once more with 100 ml of water. The organic phase was dried ($Na_2SO_4$) and concentrated under reduced pressure. The residue was admixed with 830 ml of methanol and 94.6 g of ammonium formate (1.5 mol) and then heated to reflux. After 12 h under reflux, the workup was effected by substantial concentration. The residue was taken up in 500 ml of water and extracted three times with 200 ml each time of dichloromethane. The combined organic phases were dried ($Na_2SO_4$). After the solvent had been distilled off under reduced pressure, 81 g of methyl 4-amino-5-methyl-2,5-dihydrothiophene-3-carboxylate (2) were obtained (68% of theory over all stages, content: 72.5%).

Example 4

Preparation of the Precursor of the Formula (II)

The reaction can also be conducted analogously to example 3 with chlorobenzene in place of xylene. The yield is identical to the reaction in xylene.

Example 5

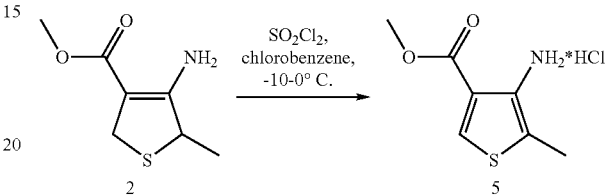

80.7 g of methyl 4-amino-5-methyl-2,5-dihydrothiophene-3-carboxylate (2) (338 mmol, content: 72.6%) were dissolved in 88 ml of chlorobenzene and cooled to −10° C. A solution of 50.2 g of sulfuryl chloride (372 mmol) in 59 ml of chlorobenzene in the temperature range of −10-0° C. was added dropwise to this solution over a period of 1 h. The reaction mixture was subsequently stirred at −10-0° C. for another 1 h and then warmed to room temperature. For workup, the reaction mixture was concentrated under reduced pressure. 95 g of methyl 4-amino-5-methylthiophene-3-carboxylate hydrochloride (5) were obtained (96% of theory, content: 58.7%, determined as the free amine). The product was characterized after release of the amine with $NaHCO_3$ solution (m.p.: 65° C.; $^1H$ NMR (400 MHz, $d^3$-DMSO): 2.62 (s), 4.25 (s), 5.18 (bs), 8.22 (s)).

Amine hydrochloride: $^1H$ NMR (400 MHz, $d^6$-DMSO): 2.44 (s), 3.83 (s), 8.21 (s)).

Example 6

11.5 g of methyl 4-amino-5-methyl-2,5-dihydrothiophene-3-carboxylate (2) (60 mmol, content: 90%) were dissolved in 25 ml of $CH_2Cl_2$ and cooled to −10° C. A solution of 8.9 g of sulfuryl chloride (66 mmol) in 10 ml of $CH_2Cl_2$ in the temperature range of −10-0° C. was added dropwise to this solution over a period of 2 h. The reaction mixture was subsequently stirred at −10-0° C. for another 1 h and then warmed to room temperature. For workup, the reaction mixture was concentrated under reduced pressure. 14.7 g of methyl 4-amino-5-methylthiophene-3-carboxylate hydrochloride (5) were obtained (89% of theory, content: 62.5%, determined as the free amine).

Example 7

5.6 g of methyl 4-amino-5-methyl-2,5-dihydrothiophene-3-carboxylate (2) (30 mmol, content: 93%) were dissolved in 30 ml of $CH_2Cl_2$. 2.3 g of chlorine (33 mmol) were introduced into this solution at room temperature over a period of 60 min. The reaction mixture was subsequently stirred for another 12 h and then, for workup, concentrated under reduced pressure. 7.2 g of methyl 4-amino-5-methylthiophene-3-carboxylate hydrochloride (5) were obtained (59% of theory, content: 42%, determined as the free amine).

What is claimed is:

1. A process for preparing a 4-alkoxycarbonyl-3-aminothiophene of formula (I)

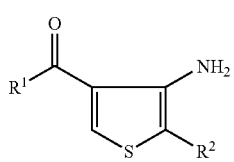

and/or a hydrochloride of the formula (I)'

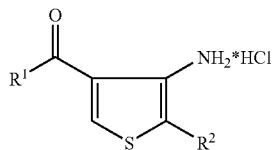

and/or a mono- or bisacetylated or mono- or bisformylated form of formulae (I)"

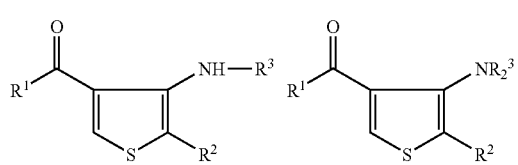

in which
R$^1$ is optionally halogen- or C$_1$-C$_4$-alkoxy-substituted alkoxy having from 1 to 6 carbon atoms,
R$^2$ is C$_1$-C$_4$-alkyl-, and
R$^3$ is an acyl or formyl substituent,
which comprises reacting
an enamine of formula (II)

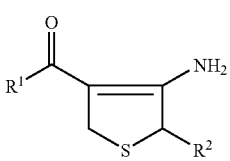

and/or a mono- or bisacetylated or mono- or bisformylated form of formula (II)"

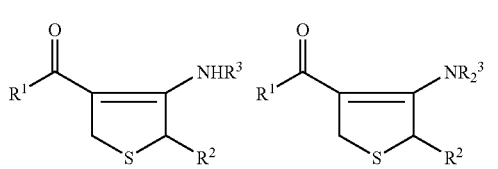

with a chlorinating agent in the presence of at least one diluent wherein the diluent is selected from the group consisting of chlorobenzene and methylene chloride.

2. The process as claimed in claim 1, wherein, in the formula (I),
R$^1$ is C$_1$-C$_4$-alkoxy,
R$^2$ is methyl, ethyl, or n- or i-propyl, and
R$^3$ is acyl or formyl.

3. The process as claimed in claim 1, wherein the process is carried out at a temperature from −15° C. to 25° C.

4. The process as claimed in claim 1, wherein the enamine of formula (II) has been obtained directly or as a precursor for an acetylated form of the formula (II)" in a preceding process step from a compound of formula (III)

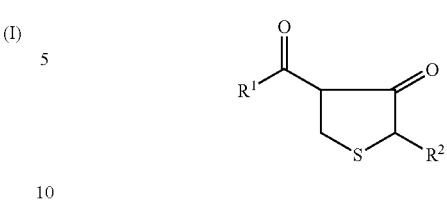

by reacting with ammonium formate, optionally in the presence of NH$_3$, with ammonium acetate, optionally in the presence of NH$_3$, with a mixture of formic acid and NH$_3$ and/or with a mixture of acetic acid and NH$_3$ in the presence of at least one diluent.

5. The process as claimed in claim 4, wherein the enamine is not isolated.

6. The process as claimed in claim 1, wherein the chlorinating agent is sulfuryl chloride.

7. A process for preparing a compound of formula (II)

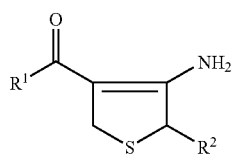

in which
R$^1$ is optionally halogen- or C$_1$-C$_4$-alkoxy-substituted alkoxy having from 1 to 6 carbon atoms,
R$^2$ is C$_1$-C$_4$-alkyl-, and
which comprises reacting a compound of formula (III)

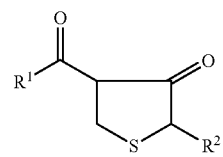

with ammonium formate, optionally in the presence of NH$_3$, with ammonium acetate, optionally in the presence of NH$_3$, with a mixture of formic acid and NH$_3$ and/or with a mixture of acetic acid and NH$_3$ in the presence of at least one diluent.

8. The process as claimed in claim 4, wherein a compound of formula (III) is reacted with NH$_3$ in the presence of a catalytic amount of ammonium formate or ammonium acetate.

9. The process as claimed in claim 8, wherein 0.1-0.8 mol of ammonium formate or ammonium acetate is used as said catalytic amount.

10. The process as claimed in claim 7, wherein compounds of formula (III) are reacted with NH$_3$ in the presence of a catalytic amount of ammonium formate or ammonium acetate.

11. The process as claimed in claim 2, wherein the reaction is carried out at a temperature from −15° C. and to 25° C.

12. The process as claimed in claim 2, wherein the diluent is selected from the group consisting of chlorobenzene and methylene chloride.

13. The process as claimed claim 1, wherein the enamine of formula (II) has been obtained directly or as a precursor for an acetylated form of the formula (II)" in a preceding process step from a compound of formula (III)

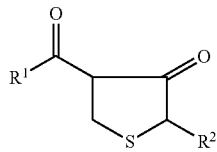
(III)

by reacting with ammonium formate, optionally in the presence of NH$_3$, with ammonium acetate, optionally in the presence of NH$_3$, with a mixture of formic acid and NH$_3$ and/or with a mixture of acetic acid and NH$_3$ in the presence of at least one diluent.

14. A process of claim 1, wherein no auxiliary base is added in said process.

15. The process as claimed in claim 1, wherein R$^2$ is methyl.

16. The process as claimed in claim 1, wherein the process is carried out at a temperature from −10° C. to 0° C.

* * * * *